United States Patent [19]

Scardera et al.

[11] 4,226,794
[45] Oct. 7, 1980

[54] LOW-FOAMING ALKOXY-BIS(TRIALKOXYSILOXY)-SILANE SURFACTANTS

[75] Inventors: Michael Scardera, Hamden; David F. Gavin, Cheshire, both of Conn.

[73] Assignee: Olin Corporation, New Haven, Conn.

[21] Appl. No.: 40,629

[22] Filed: May 21, 1979

[51] Int. Cl.³ ............................ C07F 7/04; C07F 7/18
[52] U.S. Cl. ..................................... 556/443; 252/351
[58] Field of Search ................................. 260/448.8 A

[56] References Cited

U.S. PATENT DOCUMENTS

| | | | |
|---|---|---|---|
| 2,839,558 | 6/1958 | Kirkpatrick et al. | 260/448.8 R |
| 2,990,377 | 6/1961 | May | 252/312 |
| 3,336,227 | 8/1967 | Göthel et al. | 260/448.8 A X |
| 3,965,136 | 6/1976 | Knollmueller | 260/448.8 A |
| 3,976,675 | 8/1976 | Scott et al. | 260/448.8 R |
| 4,160,776 | 10/1979 | Scardera et al. | 260/448.8 A UX |

Primary Examiner—Paul F. Shaver
Attorney, Agent, or Firm—William A. Simons; Thomas P. O'Day

[57] ABSTRACT

Novel surface active agents are disclosed having the formula:

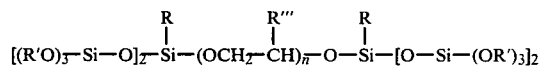

wherein R is hydrogen, an alkyl, alkenyl, aryl or aralkyl group; each R' is independently selected from the same group as R with the proviso that at least a majority of R' radicals attached to each Si atom are sterically hindered alkyl groups having at least 3 carbon atoms; each R''' independently is selected from hydrogen or methyl; and n is an integer of from about 10 to about 75.

14 Claims, No Drawings

LOW-FOAMING ALKOXY-BIS(TRIALKOXYSILOXY)-SILANE SURFACTANTS

Surfactants are commonly used agents employed in a variety of commercial products. However, while silicone oils and soaps have found wide application, silicate-based surface active agents generally have not been produced because of the inherent water instability problem encountered with these moieties. Applicants' copending U.S. Application Ser. No. 920,579, filed June 29, 1978 now U.S. Pat. No. 4,160,776 describes a novel silicate-based surfactant which overcomes this water instability problem. The surfactant defined therein features the general formula:

$$[(R'O)_3-Si-O]_2-Si-(OCH_2-\underset{\underset{R}{|}}{C}H)_n-OR''$$

wherein R is hydrogen, an alkyl, alkenyl, aryl or aralkyl group; each R' is independently selected from the same group as R with the proviso that at least a majority of R' radicals attached to each Si atom are sterically hindered alkyl groups having at least 3 carbon atoms; R" is alkyl or alkenyl having from 1 to about 20 carbon atoms; R''' is hydrogen or methyl; and n is an integer of from about 5 to about 50.

A novel silicate-based surface active agent has now been found, according to the present invention, which features favorable water stability and surface activity, and also exhibits the advantages of low-foaming properties. These surfactants have the general formula:

$$[(R'O)_3-Si-O]_2-Si-(OCH_2-\underset{\underset{R'''}{|}}{C}H)_n-O-\underset{\underset{R}{|}}{Si}-[O-Si-(OR')_3]_2 \quad \text{I}$$

wherein R is hydrogen, an alkyl, alkenyl, aryl or aralkyl; each R' is independently selected from the same group as R with the proviso that at least a majority of R' radicals attached to each Si atom are sterically hindered alkyl groups having at least 3 carbon atoms; each R''' independently is selected from hydrogen or methyl; and n is an integer from about 10 to about 75.

Desirably, R is hydrogen, an alkyl or alkenyl having about 1 to about 18 carbon atoms or an aryl or aralkyl having about 6 to about 24 carbon atoms. Preferably, R is hydrogen, an alkyl having about 1 to about 8 carbon atoms or an aryl or aralkyl having about 6 to about 14 carbon atoms. In Formula I, each R' is independently selected from the same group is R, with the proviso that at least a majority of the R' radicals attached to each Si atom are sterically hindered alkyl groups having at least 3 carbon atoms. The desired and preferred groups for R' are the same as for R, subject to the proceding proviso. Desirably, at least a majority of the R' radicals are sterically hindered alkyl groups having about 3 to about 18 carbon atoms and preferably are sterically hindered alkyl groups having about 4 to about 12 carbon atoms. Most preferably, all of the R' groups are these sterically hindered alkyl groups. By sterically hindered alkyl groups is meant alkyl radicals which contribute to the hydrolytic stability of the molecule, i.e., which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radicals and tertiary alkyl radicals. Particularly useful sterically hindered alkyl groups include sec. butyl, isobutyl, 2-ethyl butyl, 2-ethyl pentyl, 3-ethyl pentyl, 2-ethyl hexyl, 3-ethyl hexyl, 2,4-dimethyl-3-pentyl, etc. Sec. butyl is most preferred. The integer n preferably ranges from about 10 to about 75; most preferably, it ranges from about 15 to about 50. Each R''' is independently selected from hydrogen or methyl. Preferably, in about 50 to about 100 percent by weight of the groups $$-(OCH_2-\underset{\underset{R'''}{|}}{C}H)-,$$

R''' is hydrogen; more preferably in about 80 to about 100 percent of the groups, R''' is hydrogen. In a particularly preferred embodiment, in all of the groups, R''' is hydrogen.

A preferred formula for the surfactant composition of the present invention is:

$$[(CH_3-CH_2-\underset{\underset{CH_3}{|}}{C}H-O)_3-Si-O]_2-Si-(OCH_2-\underset{\underset{R'''}{|}}{C}H)_n-O-\underset{\underset{CH_3}{|}}{Si}-[O-Si-(O-\underset{\underset{CH_3}{|}}{C}H-CH_2-CH_3)_3]_2$$

wherein n and R''' are as defined above.

In a preferred method for preparing the novel silicate-based surfactants of the present invention, a polyalkoxylated linear aliphatic diol is reacted with a bis(-trialkoxysiloxy) alkylhalosilane.

The polyalkoxylated diol used in the method of the present invention has the formula:

$$H(OCH_2-\underset{\underset{R'''}{|}}{C}H)_n-OH \quad \text{II}$$

wherein R''' and n are as defined above in Formula I. This compound can be prepared by common oxyalkylation techniques. For example, it can be prepared by condensing, in the presence of an alkaline catalyst, such as KOH, a linear aliphatic diol, with ethylene oxide, or ethylene oxide and propylene oxide, in random or block arrangement. Portions of ethylene oxide in the alkoxylation mixture may range from 50 to 100 percent by weight, preferably from 80-100 percent by weight. A particularly preferred embodiment features 100 percent ethylene oxide.

The polyalkoxylated diol of Formula II above is reacted with two moles of a bis(trialkoxysiloxy) alkylhalosilane of the formula:

$$R-\underset{\underset{X}{|}}{Si}[OSi(OR')_3]_2 \quad \text{III}$$

wherein R and R' are as defined above in Formula I, and X is a halogen selected from F, Cl, Br and I. Preferably, X is Cl, Br or I; Cl is most preferred.

The compounds of Formula III are disclosed in commonly assigned U.S. Pat. No. 3,965,136 (Knollmueller) and a method for their preparation is described therein.

The disclosure of this patent is hereby incorporated in its entirety by reference.

In a preferred method of preparation, the polyalkoxylated diol compound and the bis(trialkoxysiloxy) alkylhalosilane compound are reacted in the presence of a hydrogen halide acceptor base compound. The acceptor may be any compound which will accept hydrogen halide and thereby promote the formation of the surfactant compounds of the present invention pursuant to Equation A shown below. Among the preferred acceptors are the nitrogenated tertiary organic base compounds having at least 3 carbon atoms, e.g., the lower alkyl and aryl tertiary amines such as triethylamine, tributylamine, as well as pyridine, substituted pyridine, N,N'-dimethylaniline, etc.

The formation of the novel surfactant compounds of the present invention using the above reactants may be represented by the following equation:

A

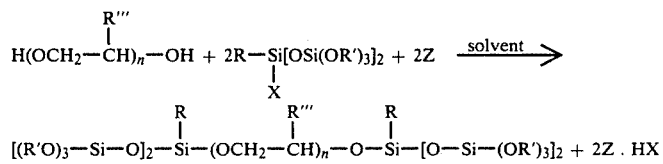

wherein Z is the hydrogen halide acceptor base and the other reactants are described above.

Equation A suggests that the principal reaction in the method of preparing the surfactant compounds of the present invention be carried out in a solvent. While the solvent is not necessary, it does serve to moderate the rate of reaction and thereby to enhance the separation of the acceptor-hydrogen halide Z.HX from the surfactant compound product. The solvent used may be any non-protonic solvent which dissolves the reactants and does not interfere with the Equation A reaction. Among the solvents which may be used are benzene, toluene, xylene, high boiling petroleum ether, other ethers such as tetrahydrofuran, and the like.

In general, a stoichiometric amount of the reactants are used. The total solvent employed in the reaction is a matter of choice and is not critical to the reaction. The hydrogen halide acceptor base also is advantageously used in a stoichiometric amount, based on the amount of bis(trialkoxysiloxy) alkylhalosilane used.

The reaction represented by Equation A may be performed at very low temperatures, room temperature, or even very high temperatures as long as there is no detrimental effect on the reactants or products. Thus, the reaction may be carried out at $-30°$ C. up to the reflux temperature of the lowest boiling constituent, and it is preferably carried out at about 0° to about 100° C. In a preferred method, the reaction is started at ambient temperature, and is completed at a higher temperature to drive the reaction as far as possible to completion. In any event, the surfactant compounds are separated from the product mixture by filtrations, distillations or other conventional separation techniques, and the particular separation system chosen merely depends upon the desired purity of the final product and its ultimate utility.

The surfactant products of this invention may be used in a variety of applications, and, in particular where low-foaming properties are required or desirable, such as in dishwashing detergent formulations, or as emulsifying agents. Also, they may be utilized in non-aqueous surfactant applications, such as in urethane foam formulations. These novel silicate-based surface active agents are unlike conventional silicate surfactants in that they exhibit favorable hydrolytic stability due to the shielding of the silicon atoms with the sterically hindered constituents, as described. The invented surfactants function similar to a silicone in reducing surface tension, and further feature the advantages of low foaming and of exhibiting oil or water solubility, depending on the particular hydrophilic moiety employed in formulating the surfactant composition.

The following examples depict preparation of the novel surfactant composition of the present invention as well as the favorable surfactant properties demonstrated thereby. The examples are intended to be illustrative and not limiting in nature.

Preparation of
Bis(Tributoxysiloxy)Methylsilane-Polyethylene Glycol
Adduct

EXAMPLE 1

In a 3-necked round bottom flask containing a magnetic stirring bar was placed 36.68 g (0.025 mole) polyethylene glycol (molecular weight 1467), 4.2 g (0.053 mole) pyridine and 50 ml toluene. The flask was fitted with a thermometer, dropping funnel, and an air condenser. Bis(tributoxysiloxy)-methylchlorosilane, 30.2 g (0.05 mole) and 50 ml toluene were mixed, placed in the dropping funnel, and gradually added to the contents of the flask with stirring at ambient temperature. Upon reaction, the white pyridine-HCl salt formed. Addition was completed in one hour, the temperature raised to 70° C. and the reaction mixture was heated an additional two hours to insure complete reaction. The reaction mixture was cooled to ambient temperature, the salt filtered off, and the clear filtrate placed on a rotary evaporator and heated to 70° C. under water aspirator vacuum for three hours to insure removal of excess pyridine and toluene solvent. The product was cooled and weighed. Product weight of the bis(tributoxysiloxy)-methylsilane-polyethylene glycol adduct was 62.45 g (theory 64.875 g, yield 99+ percent).

EXAMPLE 2

A second bis(tributoxysiloxy)-methylsilane surfactant was prepared using a procedure similar to that described in Example 1. The reactant and product specifications are set forth in Table I below.

TABLE I

| Reactants | |
|---|---|
| Polyethylene Glycol-EO Adduct | |
| Molecular Weight | 993 |
| Weight (g) | 24.835 |
| Moles | 0.025 |
| Pyridine | |
| Weight (g) | 4.2 |
| Moles | 0.053 |
| Bis(Tributoxysiloxy)-Methylchlorosilane | |
| Weight (g) | 30.2 |
| Moles | 0.05 |
| Product | |

TABLE I-continued

| | |
|---|---|
| Weight (g) | 52.22 |
| Theory (g) | 53.20 |
| Percent Yield | 98+ |

Surface properties of the products of Examples 1 and 2 are shown in Table II. The methods for determining each of the properties listed are as follows:

Cloud Point—ASTM Designation D 2024-65
Surface and Interfacial Tension—ASTM Designation D 1331-56
Draves Wetting Times—ASTM Designation D 2281-68
Ross-Miles Foam Heights—ASTM Designation D 1173-53

The reported Ross-Miles Foam Heights demonstrate the low-foaming characteristics of the invented surfactants. This test is a measure of the foam height generated initially and remaining after five minutes. The test indicates both foaming tendency as well as foam stability. The reported results generally demonstrate low initial foaming, which, in addition, is not sustained.

These surfactants also indicated excellent water solution stability as determined by surface tension measurements after standing for 60 days.

TABLE II

| Surface Tension, dynes/cm, 0.001% Solution | | |
|---|---|---|
| | Initial | After 60 Days |
| Example 1 | 27.3 | 27.6 |
| Example 2 | 28.3 | 28.5 |

| | Example 1 | Example 2 |
|---|---|---|
| Cloud Point, 1%, °C. | 75 | 0 |
| Surface Tension, dynes/cm* | | |
| 0.1% | 27.3 | 28.3 |
| 0.01 | 30.0 | 35.0 |
| 0.001 | 43.6 | 51.7 |
| Interfacial Tension, dynes/cm (vs. mineral oil) | | |
| 0.1% | 6.3 | 8.3 |
| 0.01 | 9.7 | 13.4 |
| 0.001 | 20.9 | 26.5 |
| Draves Wetting Times, secs. | | |
| @25° C. 0.5% | 83 | 17 |
| @60° C. 0.5% | 11 | 6 |
| Ross-Miles Foam, Height, mm (initial/after 5 min.) | | |
| @25° C. 0.5% | 35/30 | 25/15 |
| 0.25 | 30/25 | 25/15 |
| 0.1 | 25/20 | 20/15 |
| 0.05 | 20/15 | 15/10 |
| @60° C. 0.5% | 30/10 | 0/0 |
| 0.25 | 30/10 | 0/0 |
| 0.1 | 25/10 | 0/0 |
| 0.05 | 20/10 | 0/0 |

*For comparison, the Surface Tension of distilled water is approximately 72 dynes/cm.

We claim:

1. A low-foaming surfactant composition having the formula:

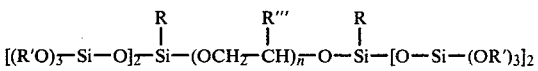

wherein n is an integer of about 10 to about 75; R is selected from hydrogen, alkyl, alkenyl, aryl, and aralkyl; each R' is independently selected from the same group as R with the proviso that at least a majority of the R' groups on each Si atom are sterically hindered alkyl groups having at least 3 carbon atoms; and each R''' is independently selected from hydrogen and methyl.

2. The surfactant composition of claim 1 wherein R is hydrogen, an alkyl or alkenyl having about 1 to about 18 carbon atoms or an aryl or aralkyl having about 6 to about 24 carbon atoms and wherein each R' is independently selected from the same group as R, subject to the above proviso.

3. The surfactant composition of claim 2 wherein a majority of the R' radicals are sterically hindered alkyl groups having about 3 to about 24 carbon atoms.

4. The surfactant composition of claim 1 wherein R is hydrogen, an alkyl having about 1 to about 8 carbon atoms or an aryl or aralkyl having about 6 to about 14 carbon atoms and wherein each R' is independently selected from the same group as R, subject to the above proviso.

5. The surfactant composition of claim 4 wherein the R' radicals are sterically hindered alkyl groups having about 4 to about 12 carbon atoms.

6. The surfactant composition of claim 1 wherein R is methyl and R' is sec. butyl.

7. The surfactant composition of claim 1 wherein n ranges from about 10 to about 30.

8. The surfactant composition of claim 7 wheren n ranges from about 15 to about 50.

9. The surfactant composition of claim 1 wherein R''' is hydrogen in about 50 to about 100 percent by weight of the alkoxy groups

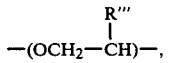

and the resulting propoxy and ethoxy groups are positioned in random or block arrangement.

10. The surfactant composition of claim 9 wherein R''' is hydrogen in about 80 to about 100 percent of the alkoxy groups.

11. The surfactant composition of claim 10 wherein R''' is hydrogen in all of the alkoxy groups.

12. The surfactant composition of claim 1 having the formula:

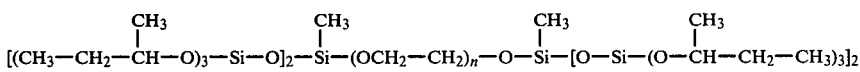

13. The surfactant composition of claim 12 wherein n is an integer from about 10 to about 75.

14. The surfactant composition of claim 13 wherein n is an integer from about 15 to about 50.

* * * * *